US00PP12951P2

(12) United States Plant Patent
Bergman

(10) Patent No.: US PP12,951 P2
(45) Date of Patent: Sep. 10, 2002

(54) CHRYSANTHEMUM PLANT NAMED 'CORAL YONASHVILLE'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 11 days.

(21) Appl. No.: 09/829,477

(22) Filed: Apr. 11, 2001

(51) Int. Cl.[7] ..... A01H 5/00
(52) U.S. Cl. ..... Plt./286
(58) Field of Search ..... Plt./286, 297

(56) References Cited

U.S. PATENT DOCUMENTS 4,616,099 A * 10/1986 Sparkes ..... 47/58

OTHER PUBLICATIONS

Shukla, et al., 1993, "Mutation studies on early and late varieties of garden chrysanthemums", J. Nuclear Agric. Biol., 22(3–4): 138–142.*

Broertjes, et al., 1980, "A mutant of a mutant of a . . . Irradiation of progressive radiation induced mutants in a mutation breeding programme with *Chrysanthemum morifolium*", Euphytica 29:525–530.*

Gosling, ed., 1979, "The Chrysanthemum Manual—6$^{th}$ edition", The National Chrysanthemum Society, London, Essex Telegraph Press, Ltd., pp. 329–336.*

Broertjes, et al., 1978, "Application of Mutation Breeding Methods in the Improvement of Vegetatively Propagated Crops," Elsevier Sci. Pub. Co., New York, pp. 162–175.*

Searle, et al., 1968, "Chrysanthemums the Year Round", Blanford Press, London, pp. 27–29, 320–327.*

Chan, 1966, "Chrysanthemum and rose mutations induced by x–rays", Am. Soc. Hort. Sci. Proc., pp. 613–620.*

Broertjes, 1966, "Mutation breeding of chrysanthemums", Euphytica, 15:156–162.*

Dowrick, et al., 1966, "The induction of mutations in chrysanthemum using x– and gamma radiation", Euphytica, 15:204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Coral Yonashville', characterized by its uniform, upright and outwardly spreading plant habit; strong and vigorous growth habit; dark green foliage, uniform flowering response; early and freely flowering habit; daisy-type inflorescences; coral pink-colored ray florets and bright yellow disc florets; and good postproduction longevity.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Coral Yonashville'.

The new Chrysanthemum is a product of a planned breeding program conducted by the Inventor in Fort Myers, Fla. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum is a naturally-occurring whole plant mutation of a proprietary induced mutation that originated by exposing unrooted cuttings of the Chrysanthemum cultivar Yonashville, disclosed in U.S. Plant Pat. No. 11,795, to X-ray radiation in October, 1997 in Fort Myers, Fla. The new Chrysanthemum was discovered and selected by the Inventor as a single flowering plant within a population of plants of the irradiated selection in April, 1998 in Fort Myers, Fla. The selection of this plant was based on its uniform plant growth habit, good vigor, desirable inflorescence form and floret colors, fast response time, and good postproduction longevity.

Asexual reproduction of the new Chrysanthemum by vegetative tip cuttings was first conducted in Fort Myers, Fla. in July, 1998. Asexual reproduction by cuttings has shown that the unique features of this new Chrysanthemum are stable and reproduced true to type in successive generations.

SUMMARY OF THE INVENTION

The cultivar Coral Yonashville has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Coral Yonashville'. These characteristics in combination distinguish 'Coral Yonashville' as a new and distinct Chrysanthemum:

1. Uniform, upright and outwardly spreading plant habit.
2. Strong and vigorous growth habit.
3. Dark green foliage.
4. Uniform flowering response.
5. Typically grown as a spray-type.
6. Early flowering, eight-week response time.

7. Freely flowering habit.

8. Daisy-type inflorescences that are about 7.1 cm in diameter.

9. Coral pink-colored ray florets and bright yellow disc florets.

10. Good postproduction longevity with plants maintaining good substance and color for about three or four weeks in an interior environment.

Plants of the new Chrysanthemum can be compared to plants of the cultivar Yonashville. In side-by-side comparisons conducted by the Inventor in Salinas, Calif., plants of the new Chrysanthemum differ from plants of the cultivar Yonashville in the following characteristics:

1. Plants of the new Chrysanthemum are slightly less vigorous than plants of the cultivar Yonashville.

2. Ray florets of plants of the new Chrysanthemum are coral pink in color whereas ray florets of plants of the cultivar Yonashville are dark lavender pink in color.

Plants of the new Chrysanthemum can be compared to plants of the Chrysanthemum cultivar Regal Yonashville, disclosed in U.S. Plant patent application Ser. No. 09/774,362. In side-by-side comparisons conducted by the Inventor in Salinas, Calif., plants of the new Chrysanthemum differ from plants of the cultivar Regal Yonashville in the following characteristics:

1. Plants of the new Chrysanthemum flower slightly earlier than plants of the cultivar Regal Yonashville.

2. Ray florets of plants of the new Chrysanthemum are coral pink in color whereas ray florets of plants of the cultivar Regal Yonashville are purple in color.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of a typical flowering plant of 'Coral Yonashville' grown a spray-type.

The photograph at the top of the second sheet comprises a close-up view of typical inflorescences of 'Coral Yonashville' grown as a spray-type.

The photograph at the bottom of the second sheet comprises a close-up view of typical inflorescences of 'Regal Yonashville' (left), the new Chrysanthemum (center) and 'Yonashvile' (right).

DETAILED BOTANICAL DESCRIPTION

In the following description, color references are made to The Royal Horticultural Society Colour Chart except where general terms of ordinary dictionary significance are used. The following observations and measurements describe plants grown and flowered during the winter in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 4,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as spray-types. Measurements and numerical values represent averages of typical flowering plants.

Botanical classification: *Chrysanthemum×morifolium* cultivar Coral Yonashville.

Commercial classification: Daisy-type potted Chrysanthemum.

Parentage: Naturally-occurring whole plant mutation of a proprietary *Chrysanthemum×morifolium* induced mutation, not patented.

Propagation:

*Type.*—Terminal tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous daisy-type potted Chrysanthemum typically grown as a spray-type. Stems upright and outwardly spreading; uniform crown. Freely branching, about three or four lateral branches develop after removal of terminal apex (pinching); dense and full plants. Vigorous.

*Plant height.*—About 24.5 cm.

*Plant width.*—About 39 cm.

*Lateral branches.*—Length: About 19.5 cm. Diameter: About 4.5 mm. Internode length: About 1.4 cm. Strength: Strong. Texture: Pubescent. Color: 144A to 146A.

*Foliage description.*—Arrangement: Alternate. Quantity of leaves per lateral stem: About 11 or 12. Length: About 8.1 cm. Width: About 4.7 cm. Apex: Cuspidate to mucronate. Base: Attenuate. Margin: Palmately lobed, sinuses between lateral lobes parallel to divergent. Texture: Upper and lower surfaces with very fine pubescence; veins prominent on lower surface. Color: Young and fully expanded foliage, upper surface: 147A. Young and fully expanded foliage, lower surface: 147B. Venation, upper and lower surfaces: Close to 147B. Petiole length: About 1.8 cm. Petiole diameter: About 3 mm. Petiole color: Close to 146C.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Typically grown as a natural or center-budded spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 49 to 55 days later when grown during the winter.

*Postproduction longevity.*—Inflorescences maintain good color and substance for about three or four weeks in an interior environment.

*Quantity of inflorescences.*—Freely flowering, about 6 inflorescences develop per lateral stem, or about 21 inflorescences per plant.

*Inflorescence bud.*—Height: About 5 mm. Diameter: About 7.5 mm. Color: More green than 146A.

*Inflorescence size.*—Diameter: About 7.1 cm. Depth (height): About 3.1 cm. Diameter of disc: About 1.5 cm. Receptacle diameter: About 5.5 mm.

*Ray florets.*—Shape: Elongated-oblong. Orientation: Initially upright, then about 45 to 50° from vertical. Aspect: Mostly flat and straight. Length: About 4.3 cm. Width: About 1 cm. Corolla tube length: About 4.5 mm. Apex: Sharply acute. Base: Attenuate; short corolla tube. Margin: Entire. Texture: Smooth, glabrous, satiny. Number of ray florets per inflorescence: About 30 arranged in two rows. Color: When opening, upper and lower surfaces: Closest to 186A to 186B. Fully opened, upper surface: Closest to 186A to 186B with slight overtones of 181C. Fully opened, lower surface: Closest to 181D to lighter than 181D.

*Disc florets.*—Arrangement: Massed at center of receptacle. Shape: Tubular, elongated. Apex: Five-pointed. Length: About 5 mm. Width: Apex: About 1.5 mm. Base: About 1 mm. Number of disc florets per inflorescence: About 92. Color: Immature: Close to 154A. Mature: Apex: 7A. Mid-section: Close to 144C. Base: 155D.

*Peduncles.*—Length: First peduncle: About 4.1 cm. Fourth peduncle: About 5.7 cm. Seventh peduncle: About 5.9 cm. Diameter: About 2 mm. Angle to vertical: About 50 to 55° from vertical. Strength: Moderately strong, flexible. Texture: Pubescent. Color: 146A.

*Reproductive organs.*—Androecium: Present on disc florets only. Anther color: 9A. Pollen: None observed. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Coral Yonashville', as illustrated and described.

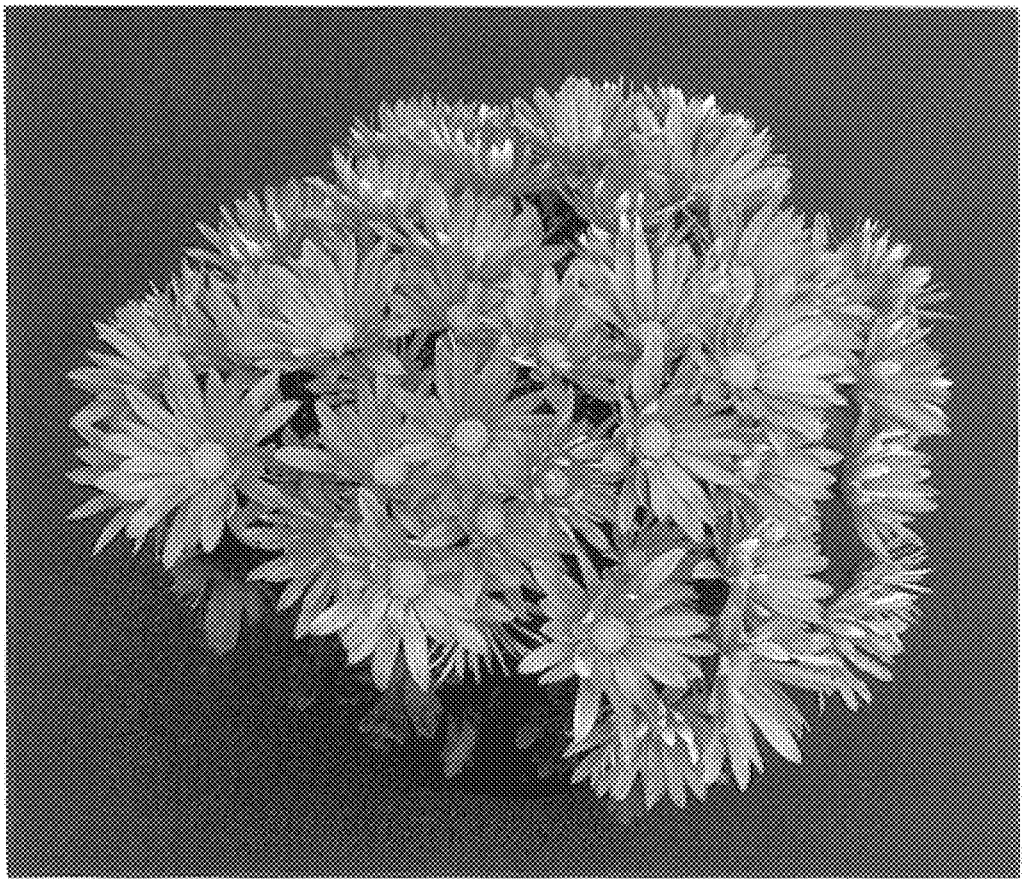

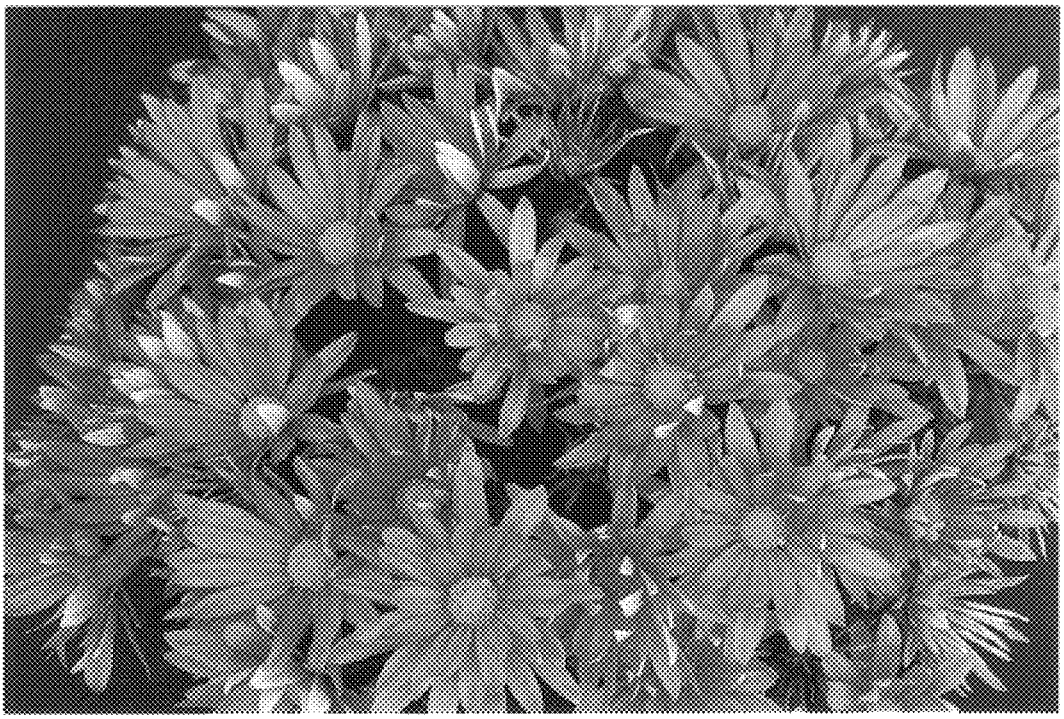
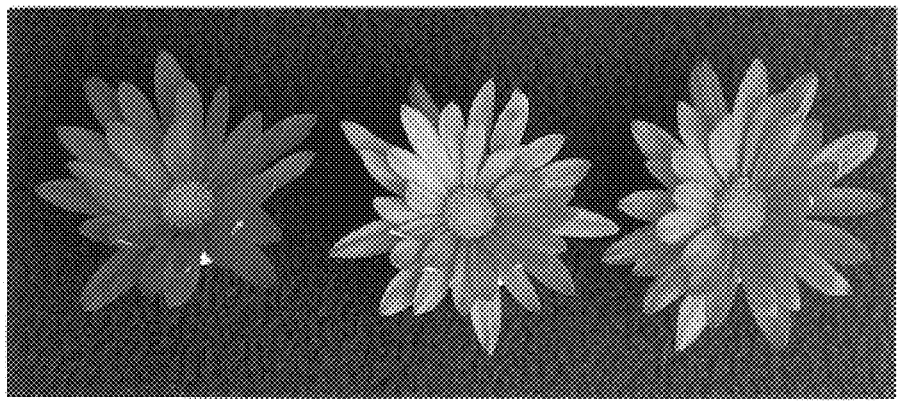

* * * * *